(12) United States Patent
Kleeman et al.

(10) Patent No.: US 6,669,668 B1
(45) Date of Patent: Dec. 30, 2003

(54) MEDICATION DELIVERY PUMP

(75) Inventors: Michael W. Kleeman, Sudbury, MA (US); David R. Brengle, San Diego, CA (US); Marc S. Lieberman, Poway, CA (US)

(73) Assignee: Tandem Medical, San Diego, CA (US)

( * ) Notice: Subject to any disclaimer, the term of this patent is extended or adjusted under 35 U.S.C. 154(b) by 0 days.

(21) Appl. No.: 09/434,974

(22) Filed: Nov. 5, 1999

(51) Int. Cl.⁷ .......................... A61M 37/00; A61M 1/00
(52) U.S. Cl. ...................... 604/131; 604/151; 417/229; 222/100; 222/101; 222/401
(58) Field of Search ................ 222/401, 100, 222/101; 604/151, 6.11, 123, 131–134, 156, 141, 65, 67, 82, 83; 128/DIG. 12, DIG. 13; 417/229

(56) References Cited

U.S. PATENT DOCUMENTS

| | | | |
|---|---|---|---|
| 3,151,616 A | * 10/1964 | Selfon | 604/131 |
| 3,198,385 A | 8/1965 | Maxwell | 222/41 |
| 3,543,966 A | 12/1970 | Ryan et al. | 222/94 |
| 3,647,117 A | 3/1972 | Hargest | 222/100 |
| 4,044,764 A | * 8/1977 | Szabo et al. | 604/134 |
| 4,525,164 A | 6/1985 | Loeb et al. | 604/131 |
| 4,557,728 A | 12/1985 | Sealfon et al. | 604/134 |
| 4,741,736 A | * 5/1988 | Brown | 604/134 |
| 4,784,157 A | 11/1988 | Halls et al. | 128/762 |
| 4,846,637 A | 7/1989 | Alderson et al. | 417/479 |
| 4,850,971 A | * 7/1989 | Colvin | 604/134 |
| 5,330,431 A | * 7/1994 | Herskowitz | 604/153 |
| 5,342,313 A | 8/1994 | Campbell et al. | 604/153 |
| 5,560,518 A | 10/1996 | Catteral et al. | 222/99 |
| 5,578,001 A | 11/1996 | Shah | 604/31 |
| 5,891,096 A | * 4/1999 | Hyun et al. | 604/131 |
| 5,954,696 A | * 9/1999 | Ryan | 604/141 |

\* cited by examiner

*Primary Examiner*—Michael J. Hayes
*Assistant Examiner*—Matthew F DeSanto
(74) *Attorney, Agent, or Firm*—Stephen E. Reiter; Foley & Lardner

(57) ABSTRACT

The present invention comprises a medication delivery pump that is configured to administer an infusion therapy using a medication delivery container. Medications in a flexible bag are expelled from the bag and delivered to an infusion site. A fluid delivery pump of the invention may have a constant force spring and a mechanical timer. The constant force spring is configured to compress a flexible fluid container. The mechanical timer assembly is coupled to the constant force spring and limits the maximum rate at which the spring compresses the fluid container. The pump may include first and second doors for charging the spring. Opening the first pump door partially charges the constant force spring and opening the second pump door fully charges the constant force spring. The pump provides improved administration of infusion therapy which is particularly advantageous for reducing errors, infections and other complications associated with manual infusion techniques.

22 Claims, 15 Drawing Sheets

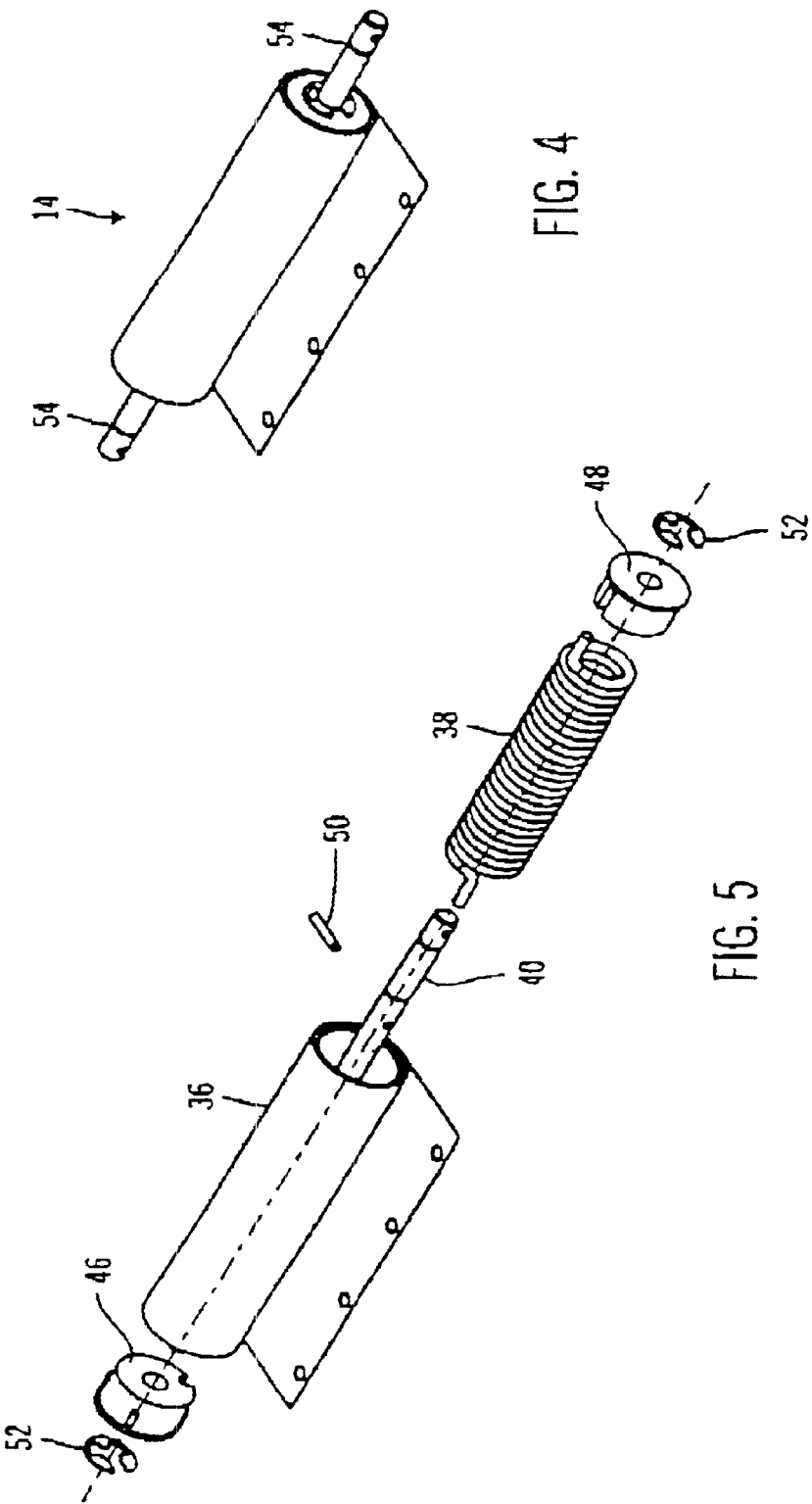

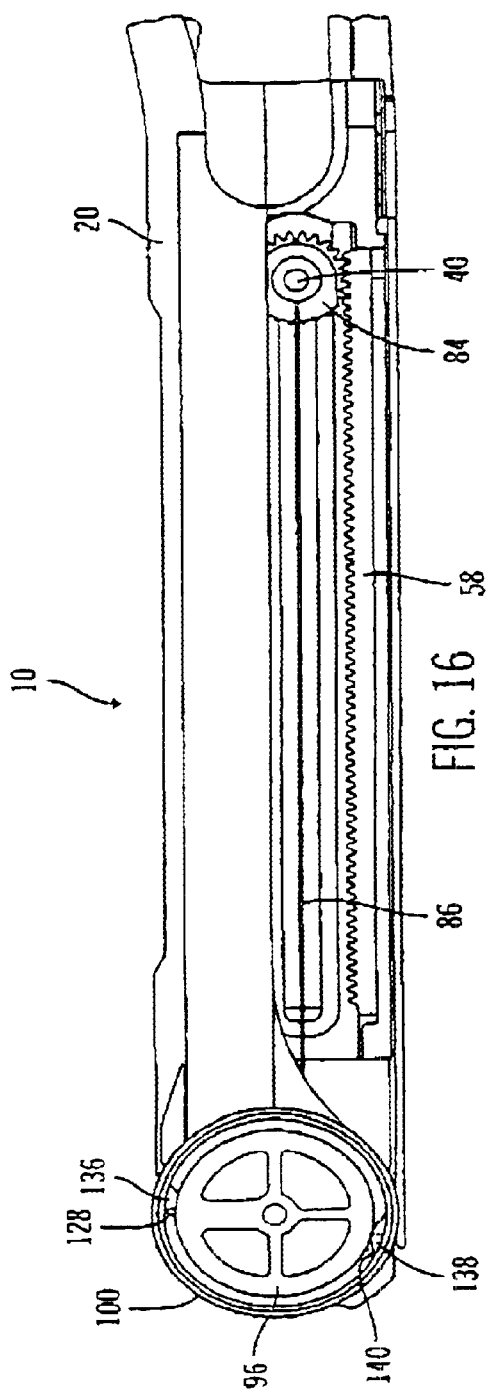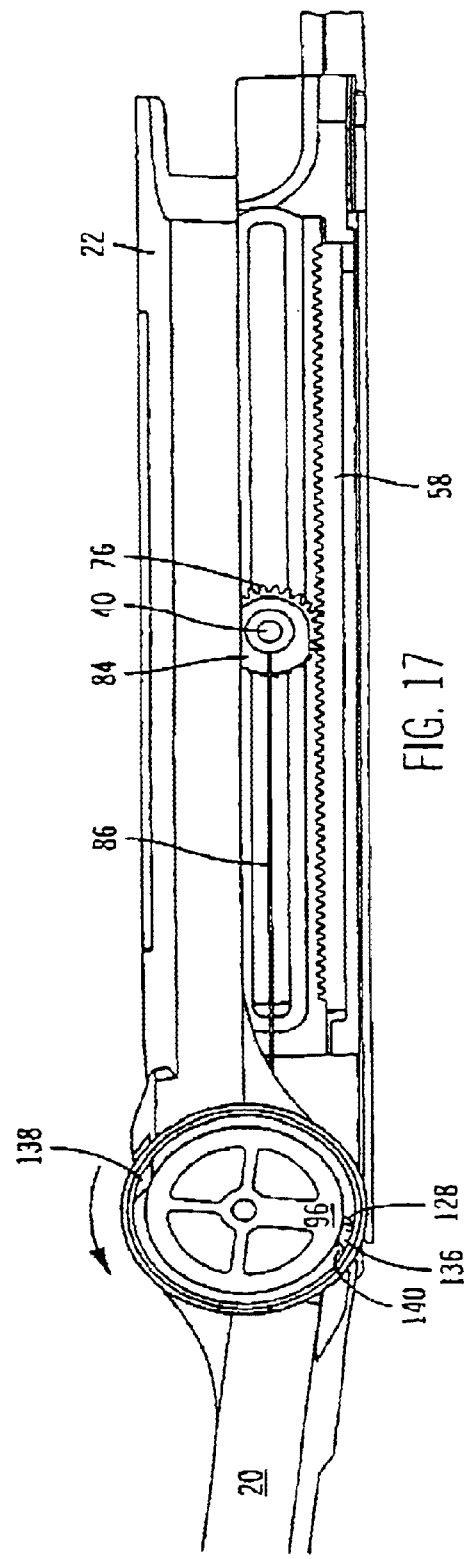

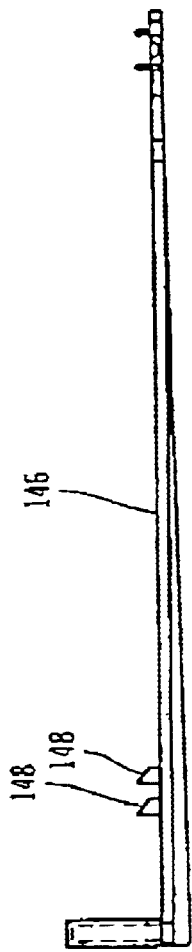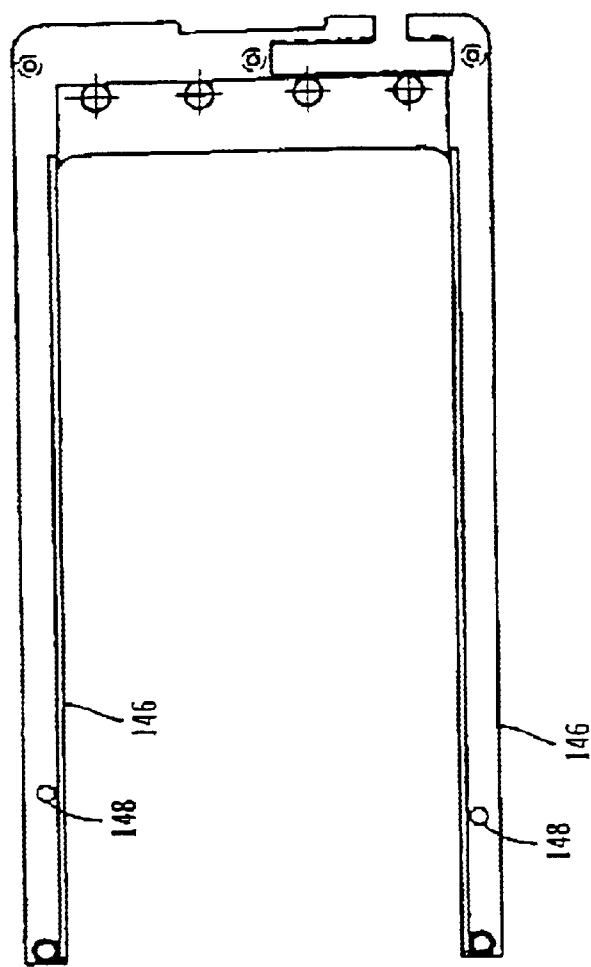
FIG. 21
FIG. 22

MEDICATION DELIVERY PUMP

FIELD OF THE INVENTION

The present invention generally relates to apparatus for the intravenous infusion of medication in accordance with a predetermined medical therapy. Medication delivery pumps of the invention are useful for improving the ease of administration of a variety of therapeutic agents.

BACKGROUND OF THE INVENTION

Intravenous medications including antibiotics and the like may be administered intermittently over a period of time. Each administration of an intravenous therapy generally follows a predefined procedure that often includes a series of manual steps. Such manual steps may include saline flushes and generally terminate with the application of anti-clotting medication. The manual steps in the therapy procedures are a principle source of error, infection, and other complications that may arise during intermittent infusion therapy.

Accordingly, there is still a need in the art for an apparatus for improving the administration of intermittent medication infusion therapy. The present invention satisfies this and other needs in the art.

BRIEF DESCRIPTION OF THE INVENTION

The present invention overcomes many of the problems in the art by providing a medication delivery pump that is configured to administer an infusion therapy using a medication delivery container. Medications in a flexible bag of the container are expelled from the bag and delivered to an infusion site. The pump provides improved administration of infusion therapy which is particularly advantageous for reducing errors, infections and other complications associated with manual infusion techniques.

The invention may be embodied in a fluid delivery pump having a constant force spring and a mechanical timer. The constant force spring is configured to compress and roll up a flexible fluid container. The mechanical timer assembly is coupled to the constant force spring and limits the maximum rate at which the spring compresses the fluid container.

In a specific embodiment of the invention, the pump includes a constant force spring and first and second doors for charging the spring. Opening the first pump door charges the constant force spring to an approximately one-half charged position and opening the second pump door charges the constant force spring to a fully charged position.

The medication delivery pump automates a number of labor steps typically used to administer multiple intravenous solutions in the proper volumes and in the proper sequence with minimal user interaction. Further, in a preferred embodiment, the pump is a mechanical device which does not require electrical energy nor software to correctly implement an infusion therapy.

BRIEF DESCRIPTION OF THE FIGURES

FIG. 4 is a perspective view of a spring assembly of the medication delivery pump of FIG. 1.

FIG. 5 is an exploded perspective view of the spring assembly of FIG. 4.

FIG. 16 is an elevation view of the medication delivery pump of FIG. 1 with a side cover removed, showing the position of a charging disk, the spring assembly and the pump's cover doors with the spring in a fully coiled or uncharged position.

FIG. 17 is an elevation view of the medication delivery pump of FIG. 1 with a side cover removed, showing the position of the charging disk, the spring assembly and the pump's cover doors with the spring in a half-coiled or half-charged position.

FIG. 21 is a plan view of a spring guard of the medication delivery pump of FIG. 1.

FIG. 22 is an elevation view of the spring guard of FIG. 21.

DETAILED DESCRIPTION OF THE INVENTION

Figure 1:
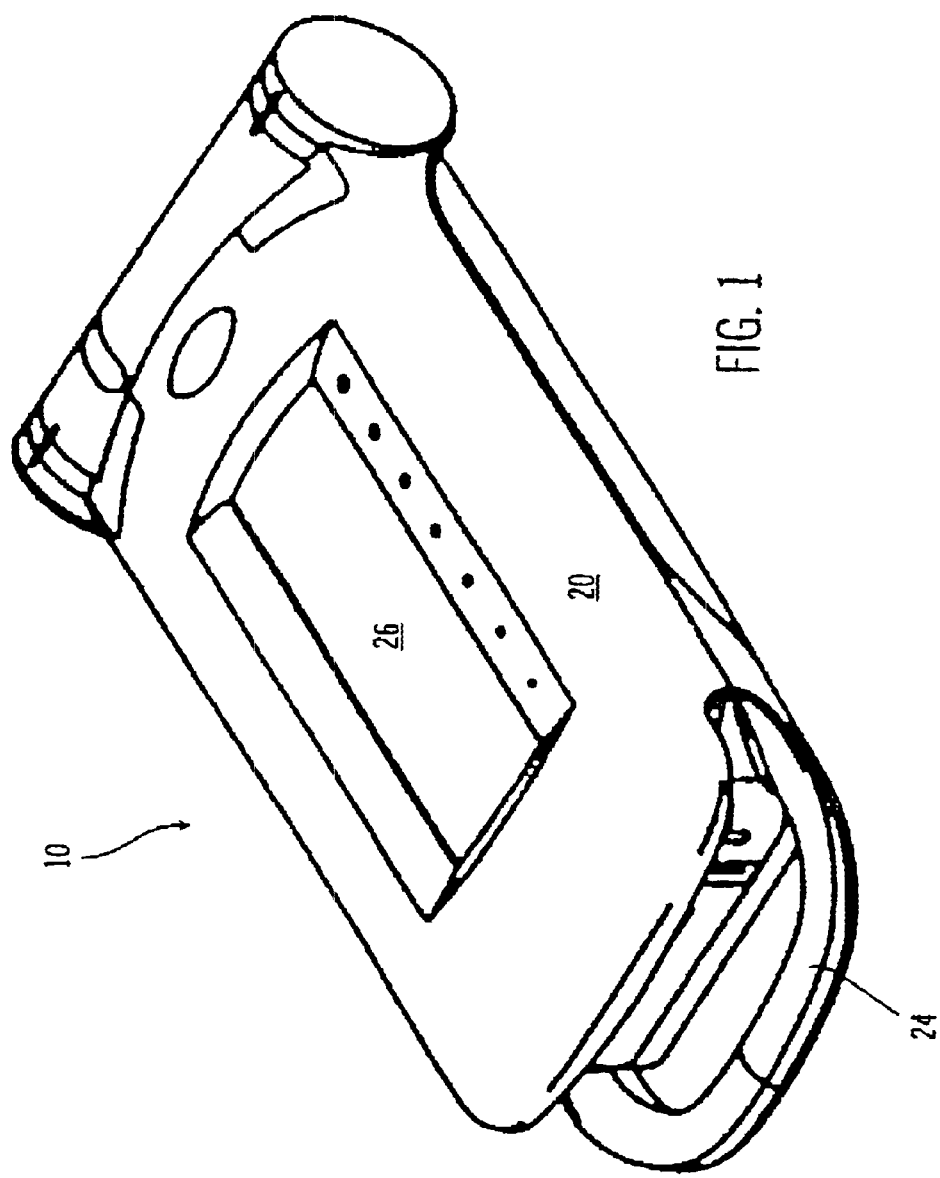
FIG. 1 is a perspective view of a medication delivery pump according to the present invention.

In accordance with the present invention, there is provided a medication delivery pump that is configured to administer an infusion therapy using a medication delivery container. The pump can be further configured to specifically interface with a medication delivery container (hereinafter, "bag") that is compartmentalized to contain multiple, separate medication solutions, and to deliver the solutions in a sequential, rate-controlled manner. Accordingly, invention pumps comprise a structure for applying constant force to a bag in a manner that sequentially activates chambers within the bag so that fluid contained therein is driven out through one or more conduits associated with each chamber, and into an intravenous (i.v.) drug delivery system (e.g., an administration set comprising microbore tubing that is attachable to a standard i.v. needle).

In one embodiment, the present invention comprises a housing for receiving and retaining a medication delivery container (bag), as described herein, during the pumping operation. The housing further contains the structure for applying constant force to the bag.

The housing can be configured to specifically receive a particular type of bag. This configuration can comprise any structure(s) that will serve to hold a specific bag in operative relationship with the mechanism for constant force. As used herein, "operative relationship with the mechanism for applying force" means that the bag is retained in a manner that allows the mechanism for applying force to activate bag chambers in the intended sequence, without displacing the bag so as to prevent correct operation. For example, the housing can include positioning pins that match holes in a medication container bag, fasteners (e.g., hook and loop, snaps, buttons, zippers, or the like) that mate with counterparts on the bag, or the like. In a particular embodiment, the housing is further configured to receive a manifold attached to the bag. By employing sufficient structure to retain the manifold, the bag is further secured.

Mechanisms for applying force contemplated for use in the practice of the present invention include force springs, a roller attached to a constant force spring, a motor-driven roller, or the like. Because a constant force spring is presently preferred, further reference to a mechanism for applying force will refer specifically to a constant force spring, with the understanding that other structures for applying force may be substituted therefor. Each such mechanism will require a different housing configuration to retain the structure and to maintain it in operative relationship with the bag during the pumping or activation process. All such housing configurations are contemplated as within the scope of the present invention.

Because it is often desirable to further control the rate at which force is applied by the constant force spring, in one embodiment, invention pumps comprise an energy absorption device. Any suitable energy absorption device may be employed. Energy absorption devices contemplated for use in the practice of the present invention include both mechanical and electrically operated devices. Mechanical devices include watchtype gear assemblies (as further described herein), watch escapements, an air resistance device, a resistance rack, an eddy current gear, a viscous damper, and the like. As used herein "watch-type gear assembly" means an assembly comprising a plurality of interconnected toothed cogs or gears that operate, in a manner known to those of skill in the art, to absorb energy by rotating and also to modulate the rate of rotation in a predictable manner. The energy absorption device can be secured to the constant force spring at its hub. Thus, the constant force spring has a maximum rate it can travel as determined by the strength of the spring, the configuration of the bag, and the amount and nature of the fluid contained in the bag. The energy absorbing device then further limits the rate at which the constant force spring can travel (i.e., work).

The invention further comprises a mechanism for charging or cocking the constant force spring. This can be accomplished in a variety of ways depending on the exact type of constant force spring employed. Because the constant force spring can be a coiled leaf of metal or other suitable material attached to a hub at the center of the coil, in one embodiment the charging mechanism will be attached to the hub. The other end of the spring is fixed to the pump housing proximal to one end of the housing. In this manner, force can be applied to the center of the hub and directed away from the fixed end of the spring, thereby causing the spring to unroll. It is presently preferred that the hub of the spring protrude from either side of the spring so that the hub can be captured in a track or like structure for retaining and guiding the travel of the constant force spring. In this manner, the travel of the spring can be controlled during charging and in performing its work. It is even more preferred that the hub have additional structure for facilitating even retraction of the spring (i.e., so that one side is not unrolled faster than the other). This can be accomplished in a variety of ways including employing a toothed gear and track assembly, as further described herein, or the like. The hub, gear and track assembly serves an additional function of providing an attachment point for the energy absorption device described herein, as well as a means to control the forward (i.e., work producing) travel of the spring.

Charging mechanisms contemplated for use in the practice of the present invention include a force transmission structure suitable for pushing or pulling the hub of the spring in the intended direction (i.e., away form the fixed end of the spring). Suitable force transmission structures include chains, belts, rods or the like, if the hub is to be pulled; and rods, or the like if the hub is to be pushed. More specifically, charging can be accomplished by employing a crank, a pneumatically operated mechanism, a plunger, a slide, or the like. It is presently preferred that the force transmission structure be connected to a mechanism for providing a mechanical advantage to the user, as the energy required to charge the constant force spring can be substantial. A mechanical advantage can be provided in the form of a lever mechanism, a multi-stage cocking mechanism, or the like. The multi-stage cocking mechanism allows partial cocking or charging of the constant force spring during each stage of the cocking. In this manner, the often substantial force required to charge the constant force spring can be parceled out over several operation stages, thereby making cocking easier than if a single stage mechanism where employed.

Advantageously, the pump will comprise an indicator such as a wheel, or the like to indicate the progress of infusion of the medication to the patient. The indicator can interface with the activating mechanism and any associated gearing to provide a true indication of the progress made by the activating mechanism. In a preferred embodiment, the indicator is geared in a manner to amplify the progress of infusion.

The invention will now be described in greater detail by reference to the following non-limiting embodiments. Moreover, each of the embodiments of the various components described below need not necessarily be used in conjunction with the other specific embodiments shown. In addition, it is contemplated that structures/devices and mechanisms that perform equivalent functions can be substituted for those described with particularity below.

Figure 2:
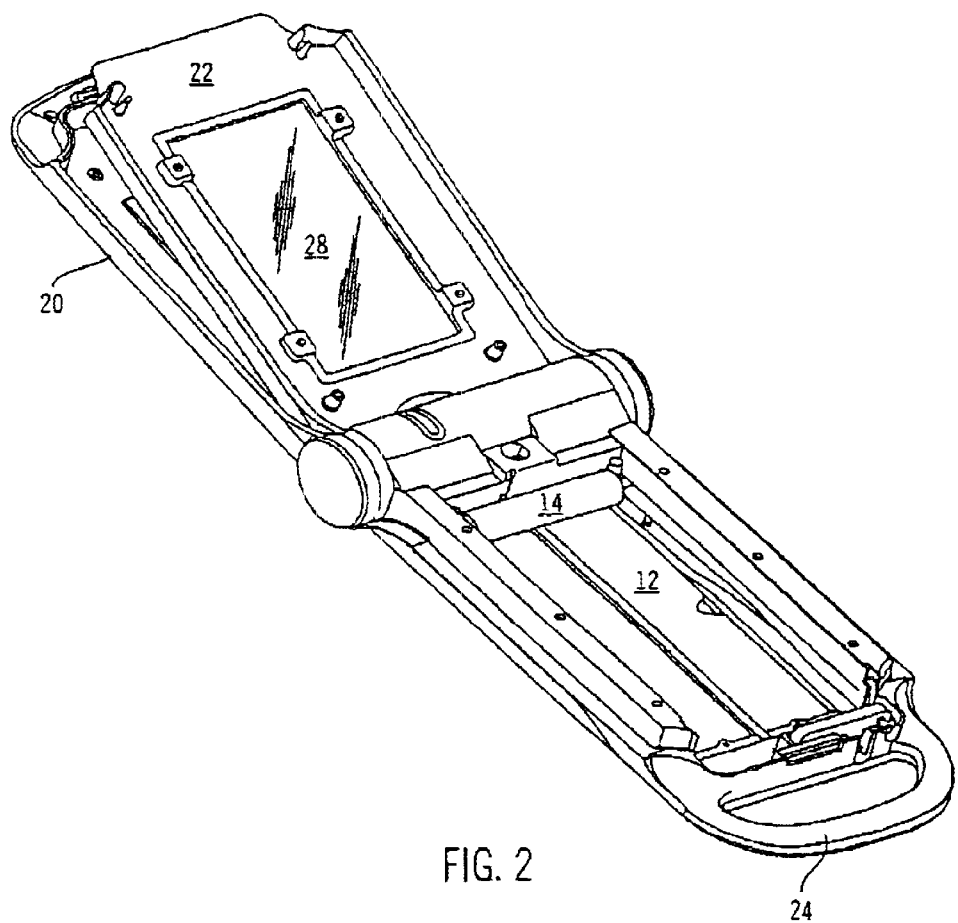
FIG. 2 is a perspective view of the medication delivery pump of FIG. 1, with the pump's cover doors in a fully opened position.
Figure 3:
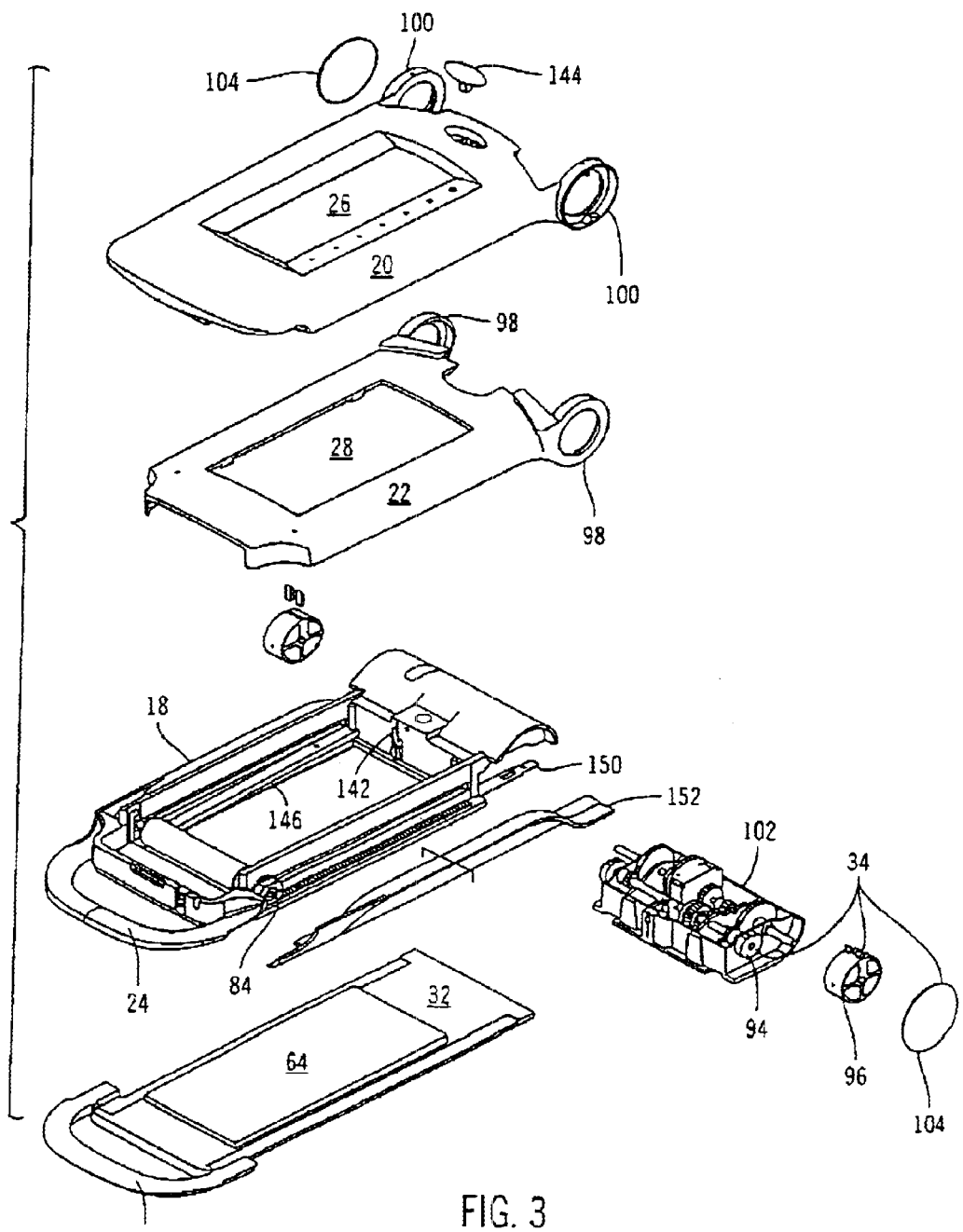
FIG. 3 is an exploded perspective view of the medication delivery pump of FIG. 1.

With reference to FIGS. 1, 2, and 3, the medication delivery pump 10 of the invention may include a receptacle 12 for receiving a bag of the medication delivery container. A spring assembly 14 in the receptacle rolls up and compresses the bag at a maximum rate controlled by an energy absorbing device in the form of a timer assembly 16. Medications in the bag's chamber(s) are expelled from the bag through a suitable exit structure, e.g., a manifold assembly, and into an administration set attached to the manifold assembly. The administration set delivers the medications to an infusion site. The pump, in combination with the container, provides improved administration of infusion therapy which is particularly advantageous for reducing errors, infections and other complications associated with manual infusion techniques.

An example of a pump in accordance with the present invention and as illustrated in FIG. 3, includes a housing having a base 18 and a pair of cover doors, 20 and 22, respectively. The cover doors are opened to provide access to the container receptacle and to charge the spring assembly. In embodiments where a two-stage, door-operated charging mechanism is not employed, a single door can be used. The pump housing, illustrated in FIGS. 1, 2 and 3, preferably includes a handle 24 for carrying the pump and to assist in holding the pump as the first and second cover doors are opened to charge the spring. The cover doors also optimally include a window or opening, 26 and 28, in each cover to allow viewing of the spring assembly and the bag in the receptacle. The base includes a container receptacle, a mechanism for applying constant force, such as a spring assembly 14, optional access points such as a bottom cover 32, a charging assembly 34 and an energy absorption device 16.

Figure 6:
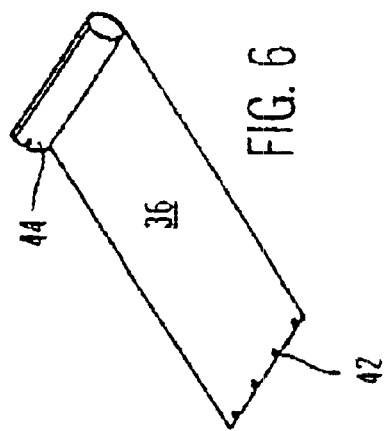
FIG. 6 is a perspective view of a constant force spring, in a stretched position, of the spring assembly of FIG. 4.
Figure 7:
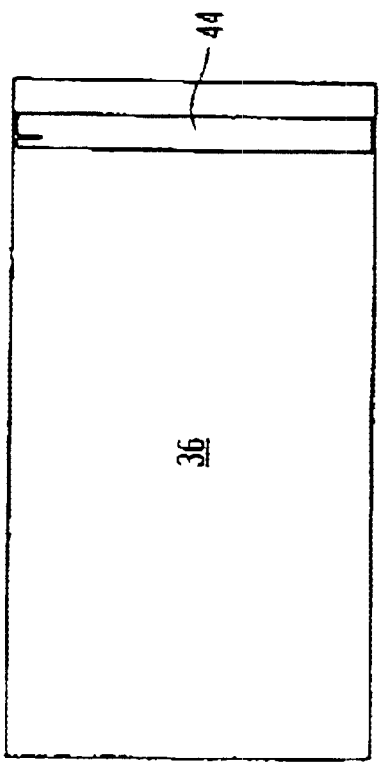
FIG. 7 is a plan view of the constant force spring of FIG. 6, in a stretched position.
Figure 8:
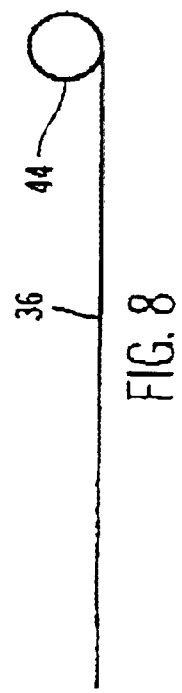
FIG. 8 is an elevation view of the constant force spring of FIGS. 6 and 7.

With reference to FIGS. 4–5, the spring assembly 14 includes a constant force pump spring 36, mechanism, such as a torsion spring 38, for keeping the constant force spring wound to provide appropriate radial force, and a pump spring shaft 40. The constant force spring, shown in FIGS. 6–8, is formed of any suitable material having resilient properties, e.g., a sheet of steel. The pump spring preferably has a structure such as holes 42 at one end for convenient attachment to the base 18. Those of skill in the art recognize that other structures for attachment can be employed such as a clamp or adhesive. A drum 44 is suitably attached, e.g., welded, to the other end of the pump spring. At rest, the pump spring is completely coiled. The torsion spring has one end connected by suitable means, e.g., a first bushing 46 to the drum inside of the pump spring. The other end of the torsion spring is connected to the shaft by a suitable device, e.g., a second bushing 48. In order to prevent the second bushing from rotating on the shaft, the bushing is attached to the shaft by a pin 50, or other suitable structure. The first and second bushings are held in place on the shaft by respective retention devices such as nuts, or, as depicted in FIG. 5, first and second e-rings 52 that engage slots on the shaft. As discussed in more detail below the torsion spring is one device that can be employed to provide radial tension on the pump spring as it compresses and rolls up the bag.

Figure 9:
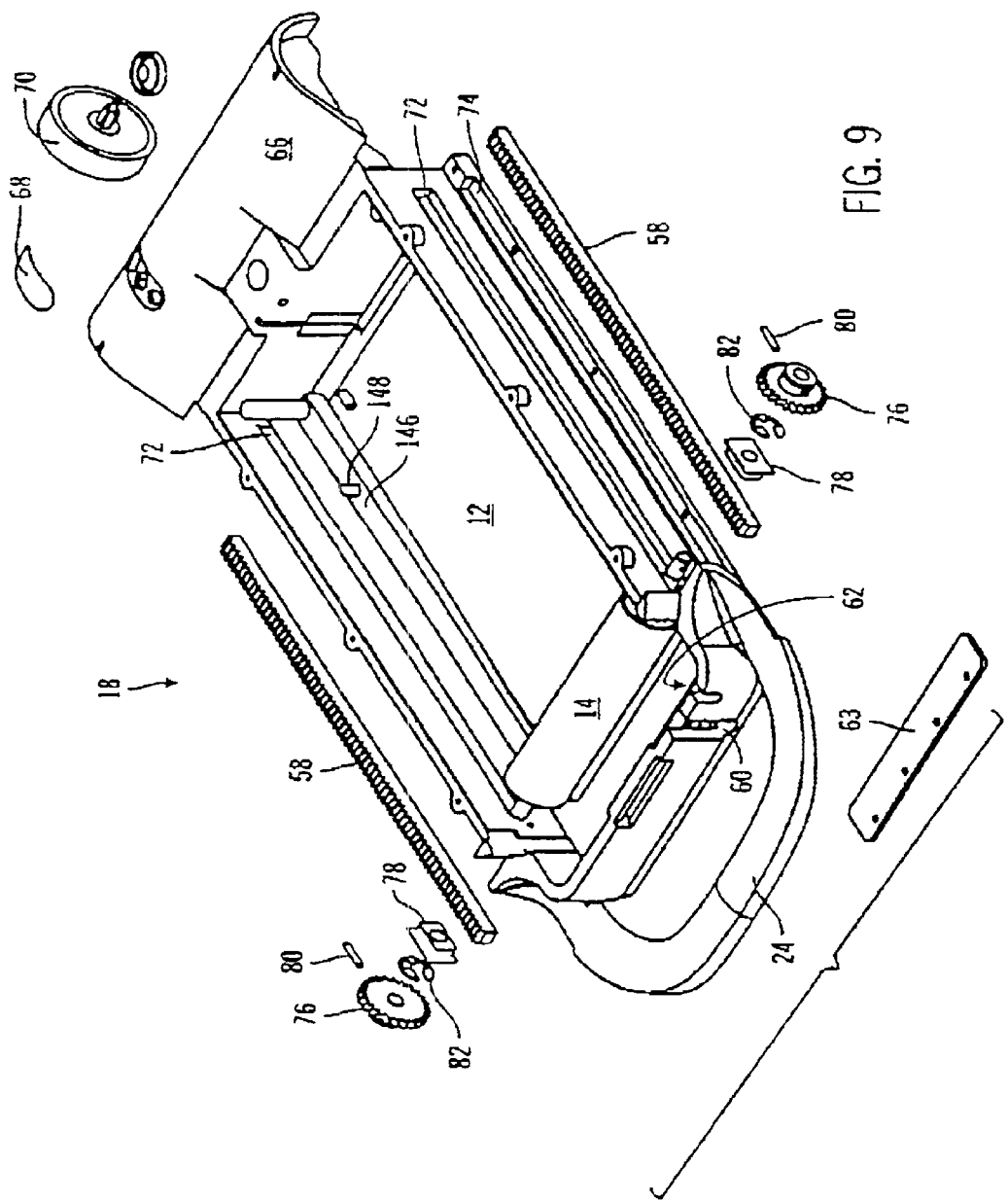
FIG. 9 is an exploded perspective view of a base assembly of the medication delivery pump of FIG. 1.

As shown in FIG. 9, the base 18 includes a frame 56 and structure (e.g., slots 72 and pair of racks 58) for retaining the pump spring hub and guiding the travel of the pump spring. The frame has at least four sides that form the sides of the container receptacle 12. At a convenient location, e.g., at a front side of the frame, is a handle 24 and a side opening to a tube exit 60. Adjacent the tube exit is a recess configured to receive a manifold assembly if one is present on the container. In the depicted embodiment, the pump spring assembly 14 has one end (opposite the drum end) attached using a plate 63 to the frame adjacent to the front side. Any manner suitable for attaching the pump spring to the housing base can be employed in the practice of the present invention.

It can be advantageous to access the components of the pump for purposes such as maintenance or adjustment; accordingly, in one embodiment of the present invention, the housing can have one or more removable portions to provide the needed access. For example, a bottom cover 32 can be removably secured to the bottom of the frame. The housing is sized to accommodate the pump spring in any state of charging. In one embodiment, the bottom (or bottom cover, when employed) has an inclined plate 64 (FIG. 3) that is tapered to accommodate an increasing spring diameter as the spring rolls up the bag. Accommodations are also included for the energy absorption device and the charging assembly. In the depicted embodiment, at the rear side of the frame is a compartment 66 for attaching the charging assembly and the timing assembly. As with other key components of the pump, it is advantageous to provide access to these components for maintenance. A window 68 is preferably provided into the compartment for viewing an indicator device, such as a wheel 70, that indicates the rate of movement of the pump spring. On two long sides of the frame are structures to receive the hub of the spring (or roller); contemplated structures are exemplified by slots 72 and adjacent ledges 74. The racks 58 are mounted on the respective ledges, or are otherwise accommodated within the housing in alternative embodiments. Side covers 152 may be employed to cover the spring gear and rack.

The constant force pump spring assembly can be retained in the housing in a variety of ways. Referring to the embodiment shown in FIG. 9, the spring assembly 14 fits in the bottom of the container receptacle with the shaft extending through the slots 72 in the long sides 56 of the frame. Located at each end of the spring shaft 40 are suitable drive structures, e.g., first and second gears 76, respectively. Other drive structures such as a bearing and race assembly, or the like, can be employed in the alternative. Structures for further retaining the spring include two horizontal slides or guide blocks 78 which are on the shaft between each gear and the pump spring and are configured to slide along the respective slots while allowing the shaft to rotate. Each gear is held on the shaft by suitable attachment devices, e.g., a pin 50 and an e-ring 52. Each gear engages the corresponding rack 58 to rotate the shaft as the spring assembly slides in the slots.

A mechanism for charging the constant force spring can be attached to the spring hub for pulling or pushing the hub away from the fixed end of the spring. In one embodiment, the charging mechanism is coupled to the spring hub by a belt assembly. In this embodiment, the hub will have sufficient structure, either as part of the hub, or attached to the hub, to facilitate secure attachment of the charging mechanism to the hub. For example, at each end of the shaft, adjacent to the respective gear (if employed), can be a belt hub 84 (FIG. 3). Each belt hub is attached to one end of a belt 86 (FIG. 16) formed of suitable material, e.g., a spring of steel. The other end of each belt is attached to the charging mechanism assembly 34. In this embodiment, the belt performs a dual purpose, i.e., both charging and rate control. The belt is also attached to the energy absorption device which controls the maximum rate at which the constant force spring can work. Thus, the energy absorption device serves to hold back, via the belt, forward progress of the constant force spring.

Figure 10:
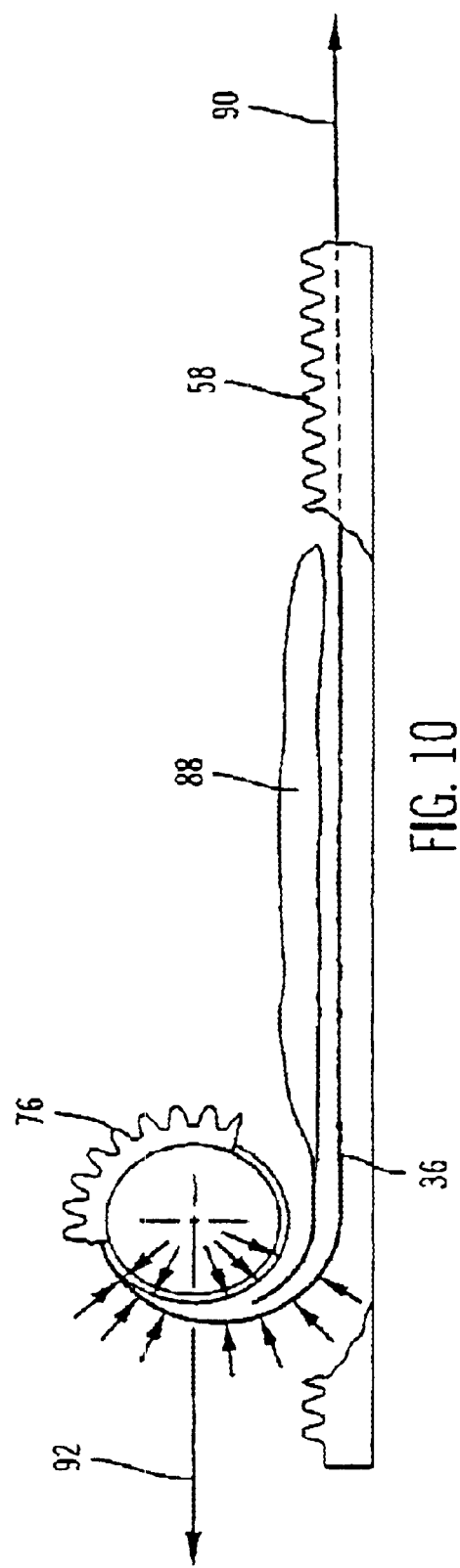
FIG. 10 is a schematic view of the spring assembly rolling up and compressing a fluid bag.

A constant force spring 36 has a tendency to roll up the bag 88 faster than the fluid may be expelled from the chambers. This is because of the fact that the hub of the spring is of fixed diameter, while the diameter of the spring changes as it rolls up. As a result, the tension on the spring can vary (i.e., lesser in the early portion of the pumping process and greater during the later portion of the spring travel), thereby allowing the spring to roll over fluid-containing chambers in the bag in the early portion of the spring travel, while possibly stalling due to increased tension in the later portion of the spring travel. Accordingly, as shown in FIG. 10, a tension force 90 may be applied to the end of the constant force spring that is distal to the hub in order to maintain the spring in a tightly coiled configuration in the early stages of the spring travel while lessening the tension in the later stages of the spring travel. It is presently preferred to have the distal end of the constant force spring fixed. Thus, in the presently preferred embodiment, a structure is provided to allow for relative motion between the hub and the constant force spring so that the constant force spring is tightened during the early stages of its travel and slackened during the later stages of its travel. The force provided by the energy absorption device can be translated to the constant force spring, while still allowing the relative motion between the hub and the spring by employing a tensioner mechanism as exemplified in FIG. 5. This figure depicts a torsion spring 38 that is internal to the drum 44. As force is applied to the hub, it is transferred to the tension spring which discourages or prevents the constant force spring from rolling over chambers of the bag that still contain fluid.

In the embodiment depicted in the attached figures, the position of an uncharged constant force spring assembly 14 is at a front or handle end of the container receptacle 12. Mechanical energy is stored in the pump spring 36 using a charging assembly 34. As discussed in more detail below, the charging assembly uses a ratchet mechanism coupled to the two cover doors, 20 and 22. Although other charging mechanisms may be employed in the practice of the present invention, a two-door ratchet mechanism is presently preferred because it reduces the force required to be applied to open a cover door during charging of the pump spring. The pump spring is pulled back a substantial portion of the distance across the receptacle, e.g., 25–75%, by opening the outer cover to an open position. The pump spring is pulled back the remaining distance by opening the inner door. Of course, other charging mechanisms can be employed, such as a wind up mechanism comprising a reduction gear, an external handle attached to a reduction gear or ratchet mechanism, or the like.

In one embodiment of the present invention, the charging assembly 34 includes the belts 86, two belt drums 94 (FIG. 3), charging disks 94, and hub rings, 98 and 100, on the cover doors, respectively. It is presently preferred, for even application of force to the spring, that the charging assembly is substantially symmetric with similar components along both sides of the pump. The components on each side of the charging assembly are coupled by a gear box assembly 102. For cosmetic and protective purposes, the charging assembly can be covered on both sides by end caps 104.

Figure 11:
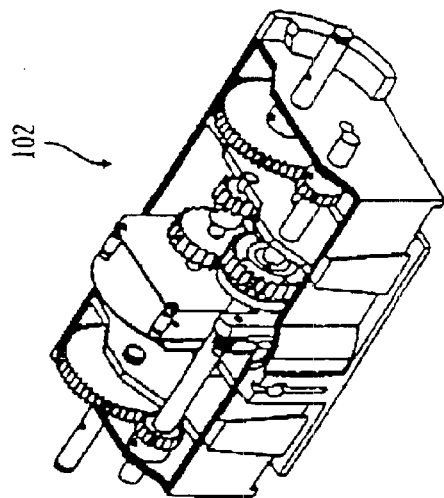
FIG. 11 is a perspective view of a gear box assembly of the medication delivery pump of FIG. 1.
Figure 12:
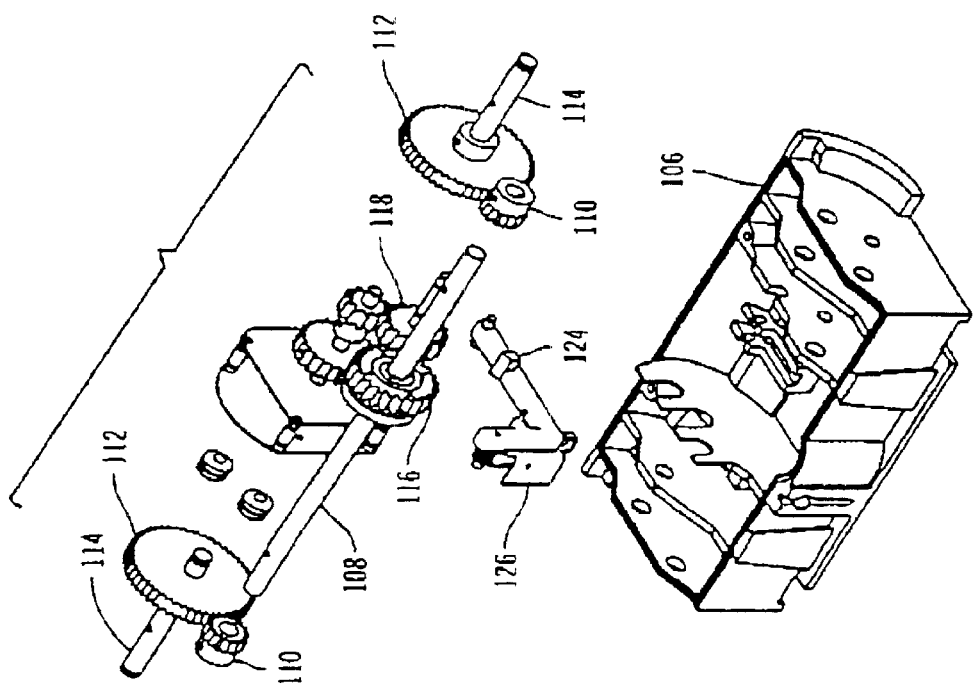
FIG. 12 is an exploded perspective view of the gear box assembly of FIG. 11.

The gear box assembly 102, shown in FIGS. 11–12, includes a gear box 106, and associated gearing to transmit force from a charging interface such as a handle, or the like, to the constant force spring. In one embodiment, the associated gearing includes a link shaft 108, first and second spur gears 110, and first and second charging gears 112 on first and second charging shafts 114, respectively. The spur gears and the charging gears will have an appropriate gear ratio for ease of operation. The ratio will, of course vary with the size of the pump apparatus and the nature of the pump spring. Presently, a ratio of approximately 3:1 is preferred. The belt drums (FIG. 3) are attached to the respective ends of the link shaft. The energy absorption assembly also resides in the gear box.

Figure 13:
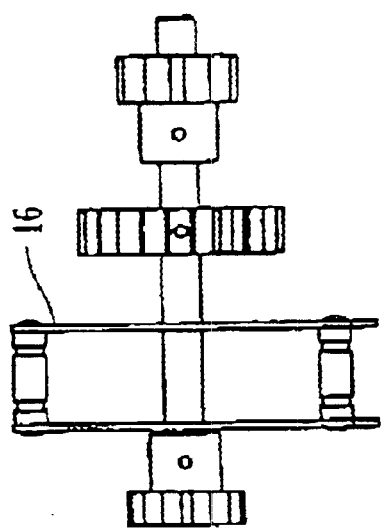
FIG. 13 is an exploded perspective view of the energy absorption device of FIG. 14.
Figure 14:
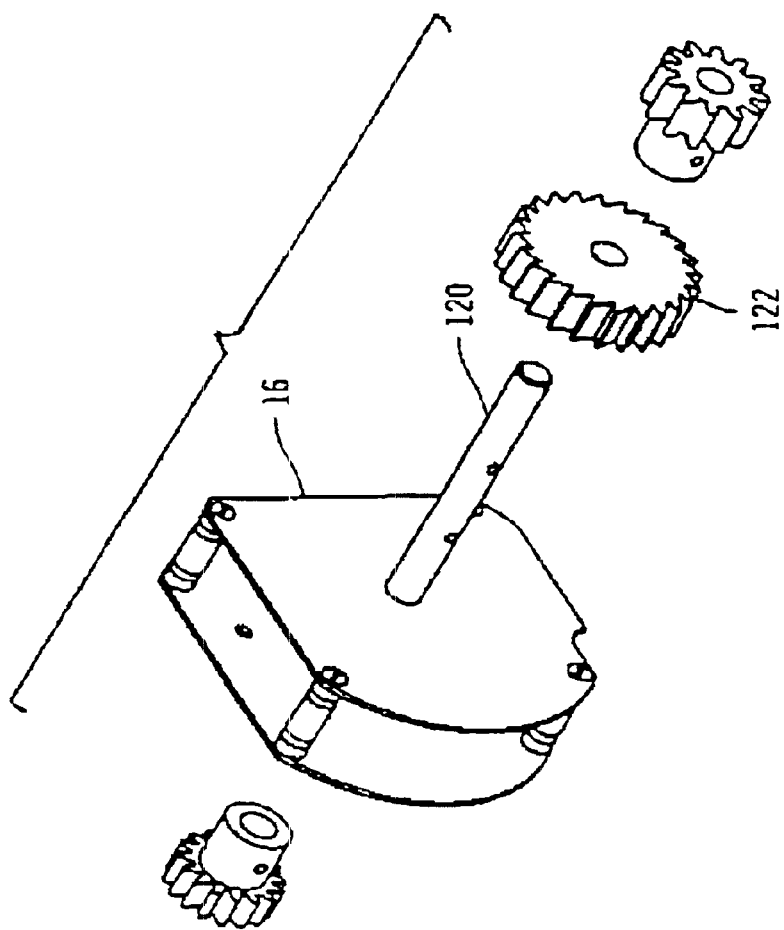
FIG. 14 is an elevation view of an energy absorption device shown in the gear box assembly of FIG. 11.

The energy absorption device/assembly 16, shown in FIGS. 13–14, controls the maximum rate at which the spring 36 may travel and compress the bag 88. Because the energy absorption assembly and the charging mechanism are both attached to the constant force spring, it is desirable to be able to disengage the energy absorption assembly during charging. Accordingly, in one embodiment, the link shaft 108 between the energy absorption assembly and the gear box assembly 102 includes a clutch assembly 116 that disengages the energy absorption assembly during charging of the pump spring. An idler gear couples the energy absorption assembly to the clutch assembly. On energy absorption assembly shaft 120 is a ratchet gear 122 that may be engaged by a start pawl 124 of the start/stop mechanism 126 to permit and halt rotation of the energy absorption assembly shaft and thus start and stop movement of the pump spring 36. Once a chamber of the bag is under compression, the fluid therein generates back pressure on the spring as it winds up on the shaft. The back pressure may limit the speed at which the spring travels. Thus, the energy absorption assembly's principle function is to limit the spring's maximum rate of travel, however, there likely will be times when the rate of spring travel is effectively limited by the fluid back pressure rather than the energy absorption device.

Figure 20:
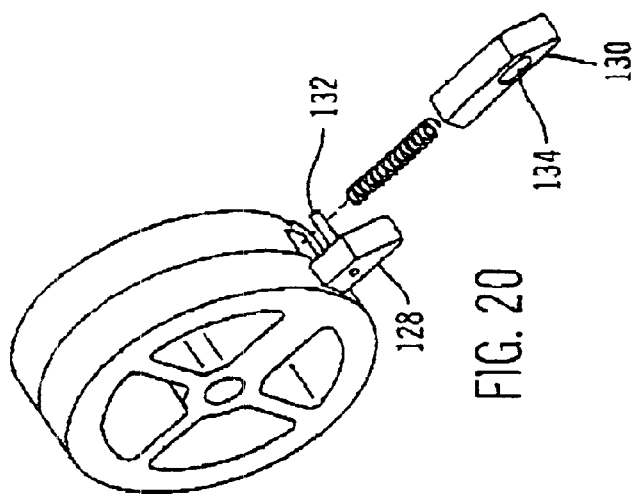
FIG. 20 is a partially exploded perspective view of the charging disk of the medication delivery pump of FIG. 1, having spring loaded pawls.

A charging disk 94, shown in FIG. 20, can be attached to the outside end of each charging shaft 114. When a two stage charging mechanism is employed, the charging disk has two catch mechanisms such as spring loaded pawls, 128 and 130, or the like. The first catch is engaged during the initial stage of the charging operation and the second catch engages during the second stage of the charging operation. When pawls are employed, at least the inner pawl has a tip beveled on one side so that a corresponding structure (e.g., the ramped tooth described below) on the hub ring (or its equivalent) can smoothly engage the pawl, while still providing a positive lock (when the non-beveled side of the pawl engages the ramped tooth). It is desirable that the shaft and slot are configured such that the inner pawl is depressed when the outer pawl is depressed; however, the outer pawl is not depressed when the inner pawl is depressed. Thus, in one embodiment, the outer pawl 128 includes a shaft 132 that engages a slot 134 on the inner pawl 130, thereby facilitating the desired operation.

Figure 15:
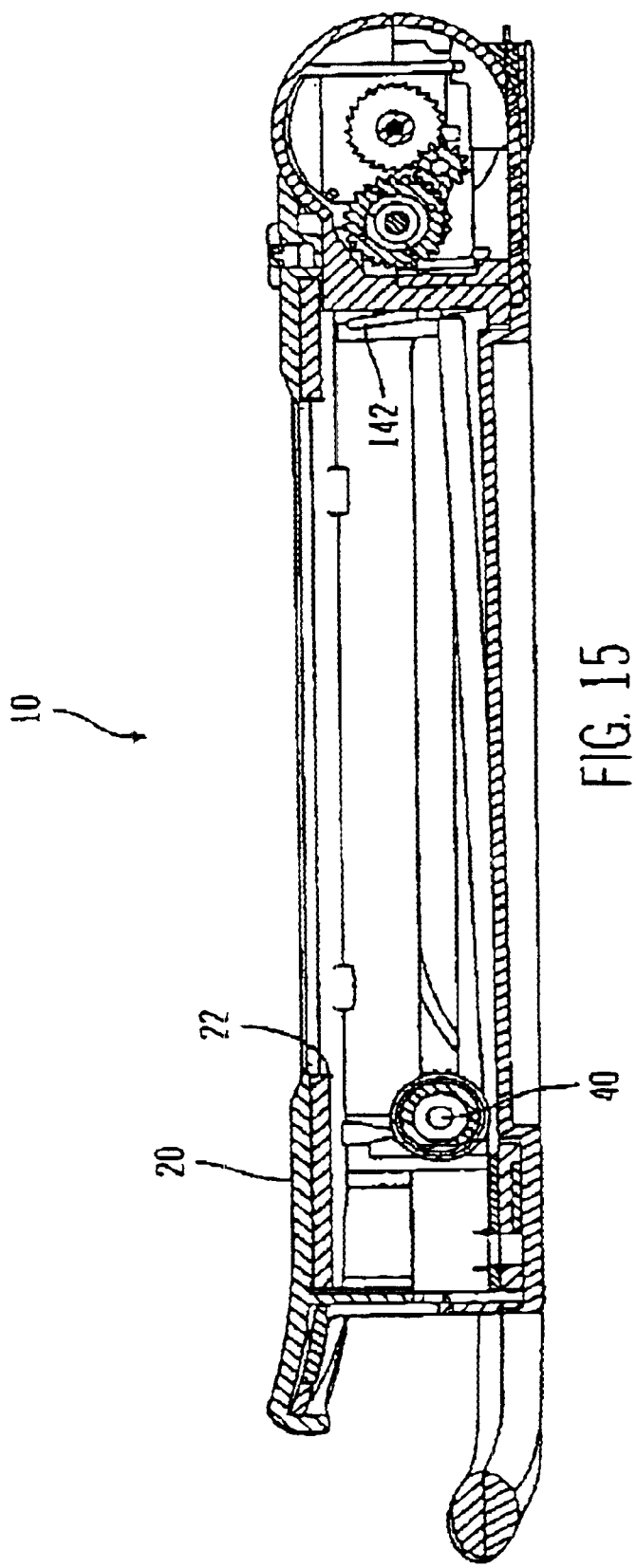
FIG. 15 is a cross-sectional side elevation view of the medication delivery pump of FIG. 1 taken through the middle of the pump.

The pump spring charging operation will now be described with reference to FIGS. 15–19. The uncharged pump is shown in FIGS. 15 and 16. In this embodiment, the pump spring 36 is at the handle end of the receptacle. The hub ring 100 of the outer cover 20 has a ramped tooth 136 and a bypass ramp 138. The ramped tooth has one side that is perpendicular to the circumference of the outer hub ring for engaging the outer pawl 128 of the charging disk during the first stage of the charging operation (i.e., by opening the outer door). Thus by opening the outer door, the outer tooth engages the outer pawl and partially rotates the charging disk, thereby partially charging the spring as shown in FIG. 17. The charging disk rotation is transferred to the belt drum 94 which winds up the belt 86 thus pulling back the spring shaft 40.

Figure 18:
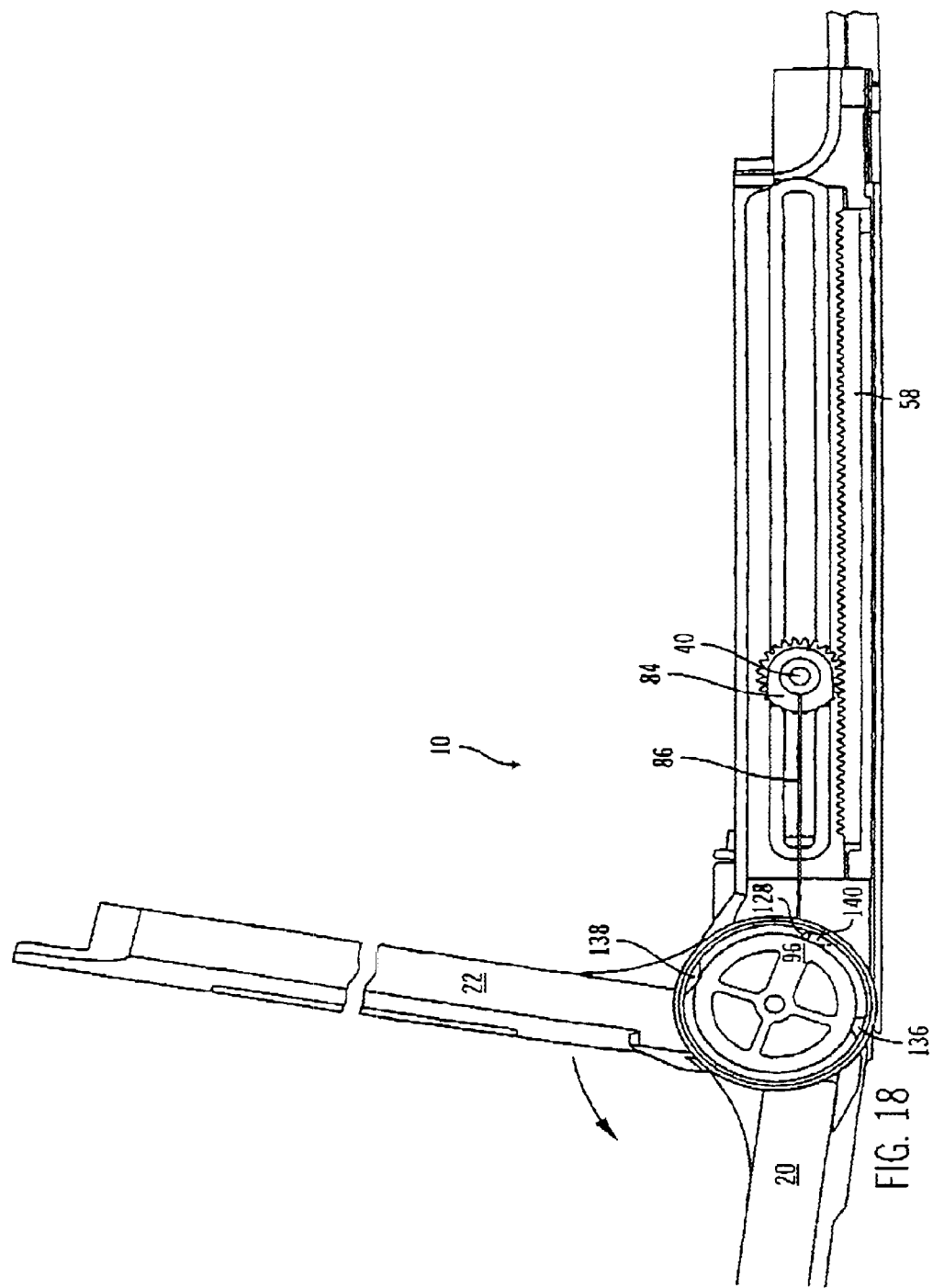
FIG. 18 is an elevation view of the medication delivery pump of FIG. 1 with a side cover removed, showing the position of the charging disk, the spring assembly and the pump's cover doors with the spring in a three-fourths uncoiled or three-fourths charged position.
Figure 19:
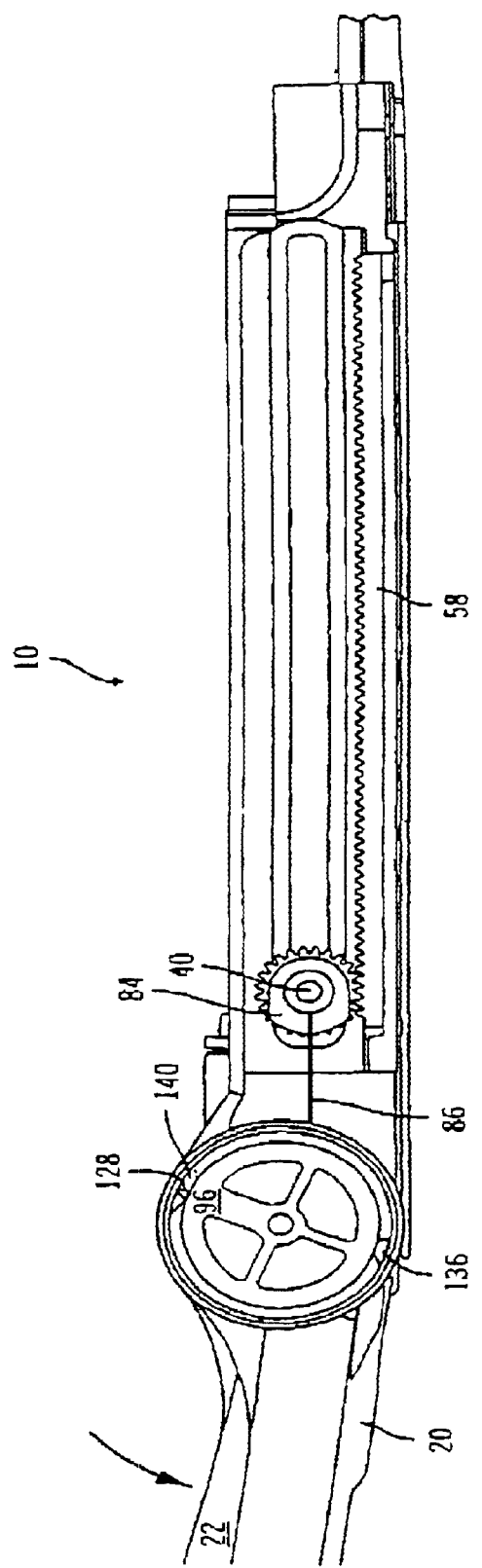
FIG. 19 is an elevation view of the medication delivery pump of FIG. 1 with a side cover removed, showing the position of the charging disk, the spring assembly and the pump's cover doors with the spring in a fully uncoiled or charged position.

As shown in FIG. 18, the inner door further rotates the charging disk resulting in further pulling of the spring shaft as follows. The hub ring 98 of the inner cover 22 also has a ramped tooth 140 having a perpendicular side for engaging the inner pawl when the inner door is opened, thereby continuing the rotation of the charging disk to complete the charging operation. The inner tooth engages the inner pawl because, as the outer door is fully opened, the beveled side of the inner tooth rides over the beveled side of the inner pawl, depressing the inner pawl 130 (not shown) to clear the inner tooth. A start/stop pawl 124 (FIG. 3) in the receptacle is automatically engaged by a ratchet wheel 22 causing the gearbox mechanism 102 to be locked into place. The bag 88 may now be placed in the pump 10 and both doors closed. A start button 144 (FIG. 3) can be activated after closing the doors. During discharge of the spring (i.e., during pumping operation), the bypass ramp 138 operates to depress the outer pawl (and, consequently, the inner pawl), thereby allowing the inner pawl to clear the inner tooth as the charging disk rotates back around in the opposite direction it rotated during charging.

The pump may include a number of features for ensuring the correct administration of the desired infusion therapy. The receptacle may have two spring guards 146, shown in FIGS. 21–22, that prevent ready access to the edges of the constant force spring 36 which tend to curl up when the spring is in the charged position. Another optional, yet presently preferred feature is an internal structure, such as a set of pins 148 on the spring guard, that mate with the bag for correct positioning of the bag in the receptacle. The pins are designed so that the bag 88 will lift off the pins as it rolls up into the spring. The, pins are offset from one another within the receptacle so that the bag can be easily placed in the receptacle in only one direction.

Interlocks can also be included so that the pump can only operate as intended. For example, a door interlock can be employed to prevent the inner door from being opened until the outer door is fully opened. The pump may also have a start button interlock 150 (FIG. 3) that detects if either of the covers are opened during the infusion. The start button engages the start/stop pawl when the door is closed, allowing the pump to operate. As a preferred safety feature, when the outer door is opened, the start button disengages from the start/stop pawl, and the pump is stopped. If the inner door is opened, the infusion is aborted. Further, the start button interlock also disables the start/stop button so that the spring motion cannot be reinitiated without recharging the puma. Aborting the infusion and disabling the start/stop button prevent improper administration caused by user interference with the bag configuration in the receptacle.

The fit and form of the pump with the doors closed is shown in the embodiment exemplified by cross-sectional diagram of FIG. 15. Corrosion resistant material may be used for those parts that may come in contact with fluids. The frame of the housing may be constructed of suitable corrosion resistant materials of sufficient rigidity, etc., e.g., polybutylene terephthalate (PBT) or similar polymer material. The rack and gears may be constructed of a metal such as brass, or the like, or a plastic material of suitable strength.

The entire disclosures of U.S. application Ser. No. 09/008, 111 and application Ser. No. 09/235,535, both titled "Medication Delivery Apparatus", and of U.S. applications titled "Medication Delivery Container" and "Medication Delivery System" both filed concurrently with this application, are incorporated herein by reference.

While the invention has been described in detail with reference to certain preferred embodiments thereof, it will be understood that modifications and variations are within the spirit and scope of that which is described and claimed.

What is claimed is:

1. A fluid delivery pump, comprising:
  a constant force spring for sequentially applying constant force to compress a flexible fluid container from a first end towards a second end of said container; and
  an energy absorption device coupled to the constant force spring for directly limiting the maximum rate at which force is applied by said constant force spring to compress the fluid container, wherein the constant force spring is coupled to a tension spring for tightly winding the constant force spring as the constant force spring compresses the flexible fluid container.

2. A fluid delivery pump according to claim 1, wherein the constant force spring is associated with a receptacle for receiving the fluid container.

3. A fluid delivery pump according to claim 2, wherein the receptacle includes structure for aligning the flexible fluid container in the receptacle.

4. A fluid delivery pump according to claim 3, wherein said structure comprises pins configured to fit in a mating set of holes in said flexible fluid container.

5. A fluid delivery pump according to claim 4, wherein the alignment pins are offset for insuring proper alignment of the flexible fluid container in the receptacle.

6. A fluid delivery pump according to claim 2, wherein the receptacle includes a bottom cover having an inclined plate for accommodating an increasing spring diameter as the constant force spring compresses the flexible fluid container.

7. fluid delivery pump according to claim 2, wherein the receptacle includes a spring guard for covering the edges of the constant force spring.

8. A fluid delivery pump according to claim 1, wherein said energy absorption device mechanically limits the maximum rate at which force is applied by said constant force siring to compress the fluid container.

9. A fluid delivery pump according to claim 8, wherein said energy absorption device is a gear assembly.

10. A fluid delivery pump, comprising: a constant force spring configured to compress a flexible fluid container, and first and second pump doors for charging the constant force spring, wherein opening the first pump door partially charges the constant force spring and opening the second pump door fully charges the constant force spring.

11. A fluid delivery pump according to claim 10, further comprising a charging assembly having first and second outer ring hubs coupled to the first pump door, first and second inner ring hubs coupled to the second pump door, and first and second charging disks each having first and second pawls, wherein the first pawls of the charging disks engage respective teeth on the outer ring hubs during opening of the first pump door and the second pawls of the charging disks engage respective teeth on the inner ring hubs during opening of the second pump door.

12. A fluid delivery pump according to claim 11, wherein said first and second spring-loaded pawls comprise a shaft that engages a slot in the second pawl, the shaft and slot being configured such that the second pawl is depressed when the first pawl is depressed and the first pawl is not depressed when the second pawl is depressed.

13. A fluid delivery pump according to claim 10, wherein the constant force spring is associated with a receptacle for receiving the fluid container.

14. A fluid delivery pump according to claim 13, wherein the receptacle includes structure for aligning the flexible fluid container in the receptacle.

15. A fluid delivery pump according to claim 14, wherein said structure comprises pins configured to fit in a mating set of holes in said flexible fluid container.

16. A fluid delivery pump according to claim 15, wherein the alignment pins are offset for insuring proper alignment of the flexible fluid container in the receptacle.

17. A fluid delivery pump according to claim 13, wherein the receptacle includes a bottom cover having an inclined plate for accommodating an increasing spring diameter as the constant force spring compresses the flexible fluid container.

18. A fluid delivery pump according to claim 13, wherein the receptacle includes a spring guard for covering the edges of the constant force spring.

19. A fluid delivery pump according to claim 10, further comprising an energy absorption device coupled to the constant force spring wherein said energy absorption device mechanically limits the maximum rate at which force is applied by said structure constant force spring to compress the fluid container.

20. A fluid delivery pump according to claim 19, wherein said energy absorption device is a gear assembly.

21. A fluid delivery pump according to claim 20, wherein said gear assembly is coupled to said constant force spring at a hub.

22. A method for charging an infusion pump having a constant force spring coupled to first and second cover doors by a charging assembly, comprising: opening the first cover door to partially charge the constant force spring; and opening the second cover door to fully charge the constant force spring.

* * * * *

UNITED STATES PATENT AND TRADEMARK OFFICE
CERTIFICATE OF CORRECTION

PATENT NO. : 6,669,668 B1
DATED : December 30, 2002
INVENTOR(S) : Kleeman et al.

It is certified that error appears in the above-identified patent and that said Letters Patent is hereby corrected as shown below:

Column 10,
Line 20, before the word "fluid" insert -- A --

Column 11,
Line 8, after the word "said" delete "structure"

Signed and Sealed this

Thirtieth Day of March, 2004

JON W. DUDAS
*Acting Director of the United States Patent and Trademark Office*